US005670358A

United States Patent [19]
Lee et al.

[11] Patent Number: 5,670,358
[45] Date of Patent: Sep. 23, 1997

[54] METHOD FOR INHIBITING CHYMOPAPAIN AND PAPAIN ENZYME ACTIVITY WITH POLYSACCHARIDES OF ANIMAL ORIGIN

[75] Inventors: Catherine T. Lee, Laguna Hills; Cynthia Zerfass, Trabuco Canyon; Tan Thanh Dinh, Garden Grove; Minh T. Ma, Santa Ana, all of Calif.

[73] Assignee: Baxter International Inc., Deerfield, Ill.

[21] Appl. No.: 545,439

[22] Filed: Oct. 19, 1995

[51] Int. Cl.$^6$ .............. C12N 9/48; C07G 17/00; C07G 15/00
[52] U.S. Cl. .............. 435/212; 435/267; 435/268; 435/381; 435/378
[58] Field of Search .............. 435/212, 219, 435/378, 381, 267, 268

[56] References Cited

U.S. PATENT DOCUMENTS

| | | | |
|---|---|---|---|
| 3,558,433 | 1/1971 | Stern | 435/219 |
| 4,142,999 | 3/1979 | Blocking et al. | 510/393 |
| 4,167,447 | 9/1979 | Masuri et al. | 435/178 |
| 4,212,945 | 7/1980 | Nonaka et al. | 435/212 |
| 4,212,946 | 7/1980 | Nonaka et al. | 435/212 |
| 4,374,926 | 2/1983 | Stern | 435/23 |
| 4,439,423 | 3/1984 | Smith | 424/94.65 |
| 4,439,521 | 3/1984 | Archer et al. | 435/381 |
| 4,652,525 | 3/1987 | Rutter et al. | 435/252.33 |
| 4,696,816 | 9/1987 | Brown | 424/94.65 |
| 4,719,108 | 1/1988 | Smith | 424/94.2 |
| 4,797,213 | 1/1989 | Parisius et al. | 210/651 |
| 4,812,314 | 3/1989 | Barenholz et al. | 424/450 |
| 4,868,121 | 9/1989 | Scharp et al. | 435/268 |
| 4,935,000 | 6/1990 | Dudek | 600/36 |
| 4,978,332 | 12/1990 | Luck et al. | 604/19 |
| 5,079,160 | 1/1992 | Lacy et al. | 435/381 |
| 5,112,757 | 5/1992 | Guguen-Guillouzo et al. | 435/347 |
| 5,116,615 | 5/1992 | Gokcen et al. | 424/94.2 |
| 5,177,017 | 1/1993 | Lin et al. | 435/252.33 |
| 5,227,157 | 7/1993 | McGinty et al. | 424/78.02 |
| 5,424,208 | 6/1995 | Lee et al. | 435/268 |

FOREIGN PATENT DOCUMENTS

| | | |
|---|---|---|
| 0 191 613 | 8/1986 | European Pat. Off. |
| 444270A1 | 12/1990 | European Pat. Off. |
| 2474-052 | 7/1981 | France . |
| 3713-197 A | 4/1987 | Germany . |
| 2064543 | 6/1981 | United Kingdom . |
| WO 89/10960 | 11/1989 | WIPO . |
| WO 91/14447 | 10/1991 | WIPO . |
| WO 94/00580 | 1/1994 | WIPO . |

OTHER PUBLICATIONS

*Journal of Supramolecular Structure*, vol. 14, No. 1, 1980, pp. 33–46, Victor B. Hatcher, et al: "Inhibition of Cell Proliferation and Protease Activity By Cartilage Factors and Heparin".

Tanaka, H., et al: "Effects of SL–1010 (Sodium Hyaluronated With High Molecular Weight) on Experimental Osteoarthritis Induced By Intra–Articularly Applied Papain in Guinea Pigs". Nippon Yakurigaku Zasshi, vol. 100, No. 1, pp. 77–86, Abstract in Medicine AN 92355006.

Kitoh, Y., et al: "Effects of Sl–1010 (Sodium Hyaluronated With High Molecular Weight) On Experimental Osteoarthritis Induced By Intra–Articularly Applied Papain In Rabbits, "Nippon Yakurigaku Zasshi, 100(1), pp.67–76, Abstract in Medicine, AN 92355005.

Valeri et al.(1980) *Biochim. Biphys. Acta*, 614(2), "Reaction of Antithrombin with Proteases Evidence for a Specific Reaction with Papain", pp. 526–533.

Alberts et al. (1983) "Molecular Biology of the Cell", Garland Publishing, Inc., New York, pp. 702–707.

C.C. Worthington, *Worthington Enzyme Manual*, "Enzymes and related biochemicals", pp. 93–95, Worthington Biochemical Corp.

M.Maeda, *Okayama Igakkai Zasshi*, 1986, "Studies on the characteristics of human lung mast cell", pp. 475–486.

I.Maruyama et al, *Journal of Pharmacol. Methods*, pp. 151–161, 1987, "Preparation of Single Smooth Muscel Cells from Guinea Pig Taenia Coli by . . . Collagenase and Papain".

B.J. Bolzon & D.W. Cheung, *Hypertension*, vol. 14, Aug. 1989, pp. 137–144, "Isolation & Characterization of Single Vasacular Smooth Muscle Cells . . .".

I.Maruyama et al., *Journal Pharmacol. Methods*, 1988, pp. 155–164, "Improvement of a Procedure for Preparing Single Smooth Muscel Cells from Guinea Pig Tenia Coli Collagenase and Papin".

E. Lammel et al, *Journal of Physicolgy*, 1991, pp.259–282, "Suppression of Steady Membrane Currents by Acetylcholine in Single Smooth Muscel Cells of the Guinea Pig Gastric Fundus".

K. Tavakol, *Surgical Forum USA*, vol. XXXVII, pp. 491–494, "Enhanced Dissolution of Nucleus Pulposus: Combined Enzyme Approach".

Kazutaka Momose, *Pharmacologica*, vol. 101, No. 3, Mar. 1993, "Isolation, configuration and contractile responses o single smooth muscle cells".

*Primary Examiner*—Jon P. Weber
*Attorney, Agent, or Firm*—Oppenheimer Poms Smith Raymond Sun

[57] ABSTRACT

The activities of chymopapain or papain in enzyme mixtures are inhibited by the addition of glycogen, hyaluronic acid, or desulfated heparin. The process for isolating viable hepatocytes or pancreatic cells by treatment with papain or chymopapain is improved by terminating the treatment by inhibiting the reaction with these polysaccharides. Similarly, the process for removing undesired tissue by treatment with papain or chymopapain is improved by terminating the treatment by inhibiting the reaction with these polysaccharides.

15 Claims, No Drawings

METHOD FOR INHIBITING CHYMOPAPAIN AND PAPAIN ENZYME ACTIVITY WITH POLYSACCHARIDES OF ANIMAL ORIGIN

BACKGROUND OF THE INVENTION

1. Field of the Invention

The present invention relates generally to proteolytic enzyme compositions and procedures for digesting connective tissue. More particularly, the present invention is directed to methods for inhibiting proteolytic enzyme activity. In one of its more particular aspects, this invention relates to methods used to ensure optimum control in reproducibly digesting connective tissue and isolating viable cells from the digested tissue.

2. Description of Relevant Art

Many cell isolation and connective tissue digestion processes utilize proteolytic enzyme compositions. Similarly, many medical procedures involve the use of proteolytic enzymes to digest and remove unwanted or undesirable tissues such as scars, burn tissue, or herniated discs. To facilitate dissociating cells from connective tissue, a sufficient amount of enzyme must be used to provide the desired degree of digestion. In order to ensure that sufficient digestion occurs, an excess of enzyme may be used.

However, the cells which are isolated may be adversely affected by certain enzymatic activity, particularly the activity of proteolytic enzymes characterized by broad specificity. Normal tissue can also be adventitiously degraded due to exposure to enzymes after each procedure. Many enzyme compositions used for cell dissociation and isolation or tissue treatment contain either chymopapain or papain. Both enzymes have activities toward a wide range of proteins.

It is necessary to stop undesired enzymatic activity as quickly as possible once the cells are dissociated from the tissues containing them, especially where isolation and purification procedures may continue for an extended period of time. Otherwise, cell integrity and function may be compromised by the continuing enzymatic degradation of cell surfaces which may result in substantial damage to the cells, such as cell membrane degradation or loss of cell surface receptors.

It is equally necessary to reduce enzymatic activity as soon as unwanted tissues are disintegrated to minimize the damage to surrounding normal tissue.

Although enzyme catalyzed reactions can, in general, be halted by separating the enzyme from the reaction mixture, by changing the pH of the reaction, or by precipitating components of the reaction, these methods may be quite drastic and cause significant changes in reaction components. It would be desirable to halt the enzymatic action in a manner which had little, if any, effect on dissociated cells or reaction components other than the enzyme or enzymes used.

Accordingly, it is an object of the present invention to provide methods for controlling proteolytic enzyme catalyzed reactions.

It is another object of this invention to provide methods for digesting connective tissue in a reproducible and controllable manner.

It is another object of the present invention to provide methods for dissociating and isolating viable cells with predictable and reproducible yields and quality.

It is a further object of the present invention to provide viable and efficacious cells for various medical uses.

It is another object of the present invention to minimize damage to other untargeted tissue components.

Further objects, features, and advantages of the present invention will become apparent to those skilled in the art from a consideration of the following detailed description.

SUMMARY OF THE INVENTION

The present invention accomplishes the above objectives by providing inhibitors of papain and chymopapain which can be used to halt or reduce enzyme activity when desired. The inhibitors of the present invention are polysaccharides of animal origin in concentrations effective to suppress papain or chymopapain enzymatic activities. The inhibitors of the present invention are highly specific in their inhibitory activity and do not inhibit other sulfhydryl proteases such as clostripain or other broad spectrum proteases such as trypsin.

It is also within the scope of the present invention to provide for isolating viable cells such as hepatocytes or pancreatic islet cells utilizing the inhibition techniques of the present invention. These processes effectively protect cells dissociated from tissue to enable the isolation of highly efficacious and viable cells in high yield.

An exemplary process of the present invention includes enzymatically digesting connective tissue by providing an enzyme composition containing papain or chymopapain, or a mixture of papain and chymopapain, in an amount sufficient to hydrolyze connective tissue and dissociate desired viable cells from such tissue. Contacting the connective tissue with the enzyme composition produces a turbid-appearing system indicating substantial tissue hydrolysis.

It is essential to halt or at least substantially slow down the enzymatic activity in the medium containing the isolated viable cells as soon as possible after the cells are dissociated from the tissue in order to preserve the cell integrity. This is accomplished by preventing excessive digestion. The enzyme inhibition process of the present invention can be utilized for this purpose. Following addition of an inhibitor in accordance with the present invention, the viability of the isolated cells is greatly reserved and the yield of viable cells is increased.

More specifically, a preferred process of the present invention utilizes the above steps following hydrolysis of connective tissue in order to protect and isolate viable cells such as hepatocytes and pancreatic islet cells. Advantageously, cells are recovered from the dissociated connective tissue in higher yield and have improved viability when compared with cells which are not protected immediately by utilizing the enzyme inhibition process of the present invention. The process of the present invention is characterized by the increased number of viable healthy cells obtained.

The increased yield, as well as increased viability and integrity of cells isolated according to the processes of the present invention, is readily demonstrated by laboratory testing techniques. Cell function and viability can be demonstrated by their biological function, such as production of insulin by pancreatic islet cells in response to glucose concentration change in culture media. This response is characterized by the ratio of insulin production in the presence of glucose to a base-line value.

The greater viability and number of useful cells isolated according to the teachings of the present invention are particularly important for applications which involve various medical procedures such as transplanting hepatocytes or pancreatic islet cells into individuals suffering from liver or pancreatic disease.

In another exemplary process, enzyme inhibition is utilized to protect normal tissue following enzymatic digestion of undesirable tissue in proximity with the normal tissue.

DESCRIPTION OF EXEMPLARY EMBODIMENTS

The present invention provides processes capable of better control in digesting physiological connective tissue in a variety of therapeutic and laboratory applications. These applications range from in vivo therapeutic treatment procedures to techniques which involve dissociating and isolating cells embedded in connective tissue for subsequent laboratory or clinical applications.

The processes of the present invention are suitable for reproducibly isolating highly viable cells from tissues made up of proteins, glycoproteins, and extracellular matrix materials. The inhibitors can also be applied to treated areas to prevent over-digestion when these enzymes are used for removal of unwanted tissues. Those skilled in the an will appreciate that the ability to carefully control the hydrolysis of a wide range of proteins and protein mixtures makes the teachings of the present invention widely applicable in a number of tissue removal treatment procedures or in vivo as well as in vitro cell isolation procedures.

The processes of the present invention find particular application in cell dissociation procedures including laboratory cell culture methods and related cell isolation techniques. As a feature of the present invention, cells are effectively and reproducibly isolated from a host of different proteinaceous connective tissues and can be harvested in higher yield with improved preservation of the cell membranes. Moreover, these cells have better viability than cells isolated using prior an processes. For this reason, the compositions and processes of the present invention are particularly suitable for isolating highly viable cells embedded in connective tissues for subsequent utility in various clinical procedures such as transplanting hepatocytes or pancreatic islet cells into individuals suffering from liver or pancreatic diseases.

Preferred exemplary embodiments of the present invention utilize enzyme solutions containing papain or chymopapain or mixtures thereof in a physiologically compatible liquid. Suitable physiologically compatible liquids include phosphate buffered saline solutions and similar buffered electrolyte solutions having osmolarities which are compatible with physiological tissue. A particularly suitable commercially available electrolyte solution is Plasmalyte® electrolyte solution available from Baxter-Hyland, having a buffered pH of 7.4 and an osmolarity of 294 mOsmol/L obtained with controlled concentrations of sodium, potassium, magnesium, chloride, acetate, and gluconate ions. Another suitable electrolyte solution is medium 199. As illustrated below, additives such as human serum albumin and serum are preferred in many applications.

Those skilled in the art will appreciate that the concentration or amount of each enzyme present in the solutions will vary with the amount and the type of tissue to be hydrolyzed. The well-known principles of enzyme activity are applicable and basic experimentation involving techniques designed to optimize enzyme concentration and total activity provide necessary information to assure the effective hydrolysis of the amount and type of selected connective tissue.

For applications directed toward digesting connective tissue and isolating hepatocytes and pancreatic islet cells embedded in the tissue, for example, exemplary compositions of the present invention may include a solution of from about 0.15 nkat/ml to about 0.55 nkat/ml purified papain or chymopapain in a suitable pH buffered physiologically compatible liquid. The nkat/ml unit is defined as nano-moles of substrate hydrolyzed per second by 1 ml of enzyme solution under the assay condition used. For purposes of the present invention, enzyme activity assays were conducted at 37° C. in Tricine buffer, 50 mM, containing 10 mM $CaCl_2$.

Chymopapain, which is a proteolytic enzyme extracted from papaya latex, is commercially available in a dry lyophilized state from a number of sources including Sigma Chemical of St. Louis, Mo. Chymopapain is available in crude, partially purified, and more highly purified forms which differ in the amount of papain, lysozyme peptidase A, and sensitizing antigens found in the preparation. Chymopapain suitable for use in the present invention is characterized as having essentially no other proteolytic enzyme contamination as a result of purification processes. Chymopapain from most commercial sources, which has been purified using known chromatographic purification processes, provides chymopapain suitable in the practice of the present invention. Alternatively, purified chymopapain can be prepared using, for example, the process described in U.S. Pat. No. 4,719,108. Papain, another papaya-derived enzyme is also commercially available. An exemplary tissue system for demonstrating the features of the present invention is connective tissue. Generally, connective tissue, which holds cells together, is a complex mixture of collagen, other extracellular proteins, glycoproteins, and mucopolysaccharides.

Thus, the processes of the present invention broadly include providing an enzyme composition and causing the composition to contact selected tissue for a length of time and at a temperature sufficient to substantially hydrolyze the tissue to remove the unwanted part or to permit isolation of the desired cells, and inhibiting the enzymatic action following sufficient tissue digestion for cell release and isolation.

Preferred exemplary processes in accordance with the teachings of the present invention include digesting connective tissue for the purpose of removing undesirable tissue or dissociating and isolating cells embedded in the connective tissue. The process of the present invention provides highly viable cells which are particularly useful for gene therapy and transplanting into humans or animals for therapeutic purposes. For example, pancreatic cells can be isolated from donor pancreases and transplanted into humans or animals for purposes of treating pancreatic related diseases. Additionally, hepatocytes can be isolated from liver in accordance with known procedures utilizing compositions of the present invention.

A most preferred process of the present invention includes providing a mixture of enzymes in which papain or chymopapain is one of the components, contacting connective tissue with the enzyme mixture for a length of time and at a temperature sufficient to substantially hydrolyze the connective tissue and to release viable cells embedded in the tissue, and immediately inhibiting the remaining enzymatic activity by adding a concentration of inhibitor sufficient to halt or substantially slow down such enzymatic activity.

The inhibitor can be added before centrifugation and pipeting off the supernatants from the cells, if desired, to reduce damage to cells during this process. Preferred exemplary processes further include rinsing the cells with a physiologically compatible liquid prior to their evaluation and use.

The inhibitors of the present invention can be characterized as polysaccharides of animal origin which have the capability of inhibiting the enzymatic activity of papain and chymopapain and which are nontoxic and otherwise compatible with viable cells. Glycogen, desulfated heparin, and hyaluronic acid are polysaccharides which have been found to exhibit these properties. All are natural components of mammalian bodies. Glycogen occurs in the liver and in rested muscle. Desulfated heparin occurs in liver and lung tissues and in most cells of several mammalian species. Hyaluronic acid occurs in the umbilical cord, in vitreous humor, in synovial fluid, and in pathologic joints. Commercially available chymopapain and papain inhibitors, which are extremely expensive, are not natural tissue components. They are toxic and may be immunogenic. Thus, they are not suitable for in vivo use.

Each of these naturally occurring polysaccharides is an effective inhibitor of papain and chymopapain activity. However, when tested against other commonly used proteases such as trypsin or clostripain, a sulfhydryl protease similar to papain and chymopapain, it was found that the enzymatic activity was either totally unaffected or affected only to a very minor extent compared to that displayed by papain and chymopapain.

The inhibitors of the present invention are nontoxic and compatible with viable cells. They can be used in cell culture, since they do not interfere with cell proliferation and function, or in vivo including use in cell transplantation.

They can be used in any concentration which does not adversely affect cell viability, cell proliferation, or cell function. In general, the more the enzymatic activity is inhibited, the more active the cells will be. Cell proliferation profiles show a dependence of cell proliferation on inhibitor concentration. Since desulfated heparin and hyaluronic acid contain acid groups, they can be used in the form of their nontoxic salts, such as the sodium, potassium, magnesium, and calcium salts of desulfated heparin or the sodium salt of hyaluronic acid. Concentrations as low as about 0.5 % desulfated heparin, 0.5 % hyaluronic acid, or 0.5 % glycogen can be used. These enzyme inhibitors can, in general, be used in the ranges of about 0.5% to 10%.

As generally mentioned above, hepatocytes and pancreatic islet cells isolated from hydrolyzed tissues in accordance with the teachings of the present invention are isolated in higher yields and have greater viability than cells isolated by prior art processes in which enzyme activity is permitted to continue, even to a limited extent, following cell isolation. Moreover, since the enzyme compositions used in the processes of the present invention are purified, in the event that isolated cells are implanted for therapeutic purposes or are subjected to other in vivo uses, any residual cotransplanted enzyme composition will not produce any adverse effect.

The superior physical and functional characteristics of the cells isolated according to the process of the present invention are demonstrated by the higher yield of cells having expected characteristics as determined by known cell-counting methods. Another technique involves use of methods in which a particular substrate is incubated with the cells to convert the substrate to a colored product. The optical density of lysed cells at 570 nm, which is proportional to the number of viable, functional cells is then determined with a spectrophotometer.

The resultant superior physical and functional characteristics of cells isolated according to the present invention make them particularly useful for transplanting. The high viability and functional ability of these cells provide a transplant that is less susceptible to functional failure.

In another embodiment of the present invention, undesirable tissue can be removed from normal tissue by the steps of providing an aqueous solution of chymopapain, papain, or a mixture thereof, in a physiologically compatible electrolyte solution buffered to a pH of about 7.0 to 7.4; contacting undesirable tissue with the enzyme solution for a length of time and at a temperature sufficient to hydrolyze the undesirable tissue; removing hydrolyzed tissue from normal tissue in contact therewith; and rinsing the normal tissue from which the undesirable tissue has been removed with a solution containing glycogen, hyaluronic acid, or desulfated heparin in a concentration sufficient to inhibit the chymopapain or papain enzymatic action.

The invention will be better understood by reference to the following nonlimiting examples which illustrate the use of the animal-derived polysaccharide materials of the present invention in inhibiting various enzymes. In these examples the activities of chymopapain and papain were determined by assay using BAPNA, N-benzoyl-L-arginine-p-nitroanilide synthetic substrate by measuring the increase in absorbance at 415 nm. The activity of clostripain was determined by assay using BAEE, N-benzoyl-L-arginine ethyl ester synthetic substrate by measuring the increase in absorbance at 253 nm. The activity of trypsin was determined by assay using BAPNA.

The following example demonstrates the reduction in activity of various enzymes in the presence of various concentrations of glycogen.

EXAMPLE 1

Protease activity was determined by measuring the reaction rates for the hydrolysis of synthetic substrates for the enzymes trypsin, chymopapain, papain, and clostripain. The increase in absorbance at 415 nm was used for the measurement of the reaction rates for trypsin, chymopapain and papain upon a BAPNA substrate. The increase in absorbance at 253 nm was used for the measurement of the reaction rates for clostripain. Trypsin, chymopapain and papain activities were determined at 37° C. in Tricine buffer, 50 mM, containing 10 mM $CaCl_2$. Clodytipain activity was determined at room temperature. Chymopapain, papain, and clostripain were activated with L-cysteine or dithiothreitol reducing agent prior to assay. Concentration of reducing agent in the substrate solution was maintained at 5 mM by addition of reducing agent to the substrate solution.

Glycogen was dissolved in the assay buffer to a final concentration of 1%. The percentage inhibition was obtained from the ratio of enzyme activity in the presence of inhibitor to the activity of a control to which no inhibitor was added. The results are shown in Table I.

TABLE I

| INHIBITION BY GLYCOGEN | | | | |
|---|---|---|---|---|
| Glycogen Concentration, % | Trypsin % Inhibited | Chymopapain % Inhibited | Papain % Inhibited | Clostripain % Inhibited |
| 0 | 0 | 0 | 0 | 0 |
| 1 | 1.1 | 17 | 12.5 | 0 |

From the foregoing data it can be seen that at a concentration of 1% glycogen had no inhibiting effect on clostripain and was only about 1% effective in inhibiting trypsin enzymatic activity. Glycogen was found to be 10-20 times as effective an inhibitor of chymopapain and papain activity as an inhibitor of trypsin activity.

The following example illustrates the reduction in activity of various enzymes in the presence of desulfated heparin.

EXAMPLE 2

The procedure of Example 1 was repeated except that a 0.5 % solution of desulfated heparin was used as the inhibitor material instead of glycogen. The results are shown in Table II.

TABLE II

INHIBITION BY DESULFATED HEPARIN

| Desulfated Heparin Concentration, % | Trypsin % Inhibited | Chymopapain % Inhibited | Papain % Inhibited | Clostripain % Inhibited |
|---|---|---|---|---|
| 0 | 0 | 0 | 0 | 0 |
| 0.5 | 4.1 | 8.8 | 9.8 | 0.8 |

The foregoing results show that at a concentration of 0.5 % desulfated heparin was only about one-tenth as effective in inhibiting clostripain as chymopapain and papain and less than one-half as effective in inhibiting trypsin as chymopapain and papain.

The following example illustrates the reduction in activity of various enzymes in the presence of hyaluronic acid.

EXAMPLE 3

The procedure of Example 1 was repeated except that a 0.5% solution of hyaluronic acid was used as the inhibitor instead of glycogen. The results are shown in Table III.

TABLE III

INHIBITION BY HYALURONIC ACID

| Hyaluronic Acid Concentration, % | Trypsin % Inhibited | Chymopapain % Inhibited | Papain % Inhibited | Clostripain % Inhibited |
|---|---|---|---|---|
| 0 | 0 | 0 | 0 | 0 |
| 0.5 | 0 | 34.2 | 35.8 | 0 |

These results show that at a concentration of 0.5 % hyaluronic acid had no inhibiting effect on trypsin or clostripain but was effective in inhibiting chymopapain and papain.

Having thus described preferred exemplary embodiments of the present invention, it should be noted by those skilled in the art that the disclosures herein are exemplary only and that alternatives, adaptations, and modifications may be made within the scope of the present invention. Accordingly, the present invention is not limited to the specific embodiments illustrated herein.

What is claimed is:

1. A process for inhibiting the activity of an enzyme selected from the group consisting of chymopapain and papain which comprises adding a polysaccharide selected from the group consisting of glycogen, desulfated heparin, and hyaluronic acid to a medium containing said enzyme, said polysaccharide being added in a concentration effective to inhibit the activity of said enzyme.

2. The process of claim 1 wherein said concentration is about 0.5% to 10%.

3. The process of claim 1 wherein said polysaccharide is glycogen.

4. The process of claim 1 wherein said polysaccharide is desulfated heparin.

5. The process of claim 1 wherein said polysaccharide is hyaluronic acid.

6. A process for isolating viable hepatocytes or pancreatic islet cells from tissue containing viable hepatocytes or pancreatic islet cells, said process comprising the steps of:

providing an enzyme composition comprising an aqueous solution of an enzyme selected from the group consisting of chymopapain, papain, and mixtures thereof, said enzyme having an activity of about 0.15 nkat/ml to about 0.55 nkat/ml, in a physiologically compatible electrolyte solution buffered to a pH of about 7.0 to 7.4;

contacting tissue containing viable hepatocytes or pancreatic islet cells with said enzyme for a length of time and at a temperature sufficient to hydrolyze said tissue;

isolating viable hepatocytes or pancreatic islet cells from the hydrolyzed tissue; and adding a polysaccharide selected from the group consisting of glycogen, desulfated heparin, and hyaluronic acid to a medium containing the isolated viable hepatocytes or pancreatic islet cells, said polysaccharide being added in a concentration sufficient to inhibit the enzymatic action of said chymopapain or papain or mixture of chymopapain and papain;

thereby improving the yield of viable hepatocytes or pancreatic islet cells and enhancing the cell activity thereof.

7. The process of claim 6 wherein said concentration is about 0.5% to 10%.

8. The process according to claim 6, wherein said polysaccharide is glycogen.

9. The process according to claim 6, wherein said polysaccharide is desulfated heparin.

10. The process according to claim 6, wherein said polysaccharide is hyaluronic acid.

11. A process for removing undesirable tissue from normal tissue, comprising the steps of:

providing an enzyme composition comprising an aqueous solution of an enzyme selected from the group consisting of chymopapain, papain, and mixtures thereof, in a physiologically compatible electrolyte solution buffered to a pH of about 7.0 to 7.4;

contacting tissue containing undesirable tissue in contact with normal tissue with said enzyme composition for a period of time and at a temperature sufficient to hydrolyze said undesirable tissue;

removing hydrolyzed undesirable tissue from said normal tissue; and rinsing the normal tissue from which the undesirable tissue has been removed with a solution containing a polysaccharide selected form the group consisting of glycogen, desulfated heparin, and hyaluronic acid, said polysaccharide being present in a concentration sufficient to inhibit the enzymatic action of said chymopapain or papain or mixture of chymopapain and papain.

12. The process of claim 11 wherein said concentration is about 0.5% to 10%.

13. The process according to claim 11, wherein said polysaccharide is glycogen.

14. The process according to claim 11, wherein said polysaccharide is desulfated heparin.

15. The process according to claim 11, wherein said polysaccharide is hyaluronic acid.

* * * * *